(12) United States Patent
Hoenes et al.

(10) Patent No.: US 9,757,059 B2
(45) Date of Patent: Sep. 12, 2017

(54) INTEGRATED TEST ELEMENT

(75) Inventors: Joachim Hoenes, Zwingenberg (DE); Karl Miltner, Frankenthal (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1586 days.

(21) Appl. No.: 10/559,547

(22) PCT Filed: Jun. 2, 2004

(86) PCT No.: PCT/EP2004/005924
§ 371 (c)(1),
(2), (4) Date: Jan. 13, 2006

(87) PCT Pub. No.: WO2004/107970
PCT Pub. Date: Dec. 16, 2004

(65) Prior Publication Data
US 2006/0229533 A1    Oct. 12, 2006

(30) Foreign Application Priority Data
Jun. 6, 2003 (DE) .................................. 103 25 699

(51) Int. Cl.
*A61B 5/00* (2006.01)
*A61B 5/1459* (2006.01)
(Continued)

(52) U.S. Cl.
CPC ........ *A61B 5/1459* (2013.01); *A61B 5/14532* (2013.01); *A61B 5/157* (2013.01);
(Continued)

(58) Field of Classification Search
CPC ....... A61B 5/145; A61B 5/15; A61B 5/14532; A61B 5/1455; A61B 5/150022;
(Continued)

(56) References Cited

U.S. PATENT DOCUMENTS 3,878,830 A * 4/1975 Bicher .......................... 600/360
4,360,016 A    11/1982 Sarrine
(Continued)

FOREIGN PATENT DOCUMENTS

| | | |
|---|---|---|
| EP | 0 409 033 A2 | 1/1991 |
| EP | 1 416 263 A2 | 5/2004 |

(Continued)

OTHER PUBLICATIONS

Tutorial review—Optical chemical sensors: transduction and signal processing Ramaier Narayanaswamy Analyst, 1993,118, 317-322.*

*Primary Examiner* — Patricia Mallari
*Assistant Examiner* — Karen Toth
(74) *Attorney, Agent, or Firm* — Woodard, Emhardt, Moriarty, McNett, & Henry LLP

(57) ABSTRACT

The invention relates to the field of integrated systems which comprise a test element and a lancet which can be firstly used to make a wound in a skin opening in order to collect a sample. The sample is subsequently directly taken up by the test element in the process of which it comes into contact with a reagent contained in the test element and results in an optically detectable change in a test field. The change in the test field is detected by means of an analytical unit which is optically contacted with the test field via at least one light-conducting element.

26 Claims, 4 Drawing Sheets

(51) Int. Cl.
*A61B 5/145* (2006.01)
*G01N 21/03* (2006.01)
*G01N 21/64* (2006.01)
*G01N 21/77* (2006.01)
*A61B 5/15* (2006.01)
*A61B 5/157* (2006.01)
*A61B 5/1455* (2006.01)
*A61B 5/151* (2006.01)

(52) U.S. Cl.
CPC .. *A61B 5/150022* (2013.01); *A61B 5/150358* (2013.01); *A61B 5/150389* (2013.01); *A61B 5/150503* (2013.01); *A61B 5/150572* (2013.01); *A61B 5/150824* (2013.01); *A61B 5/6848* (2013.01); *G01N 21/03* (2013.01); *G01N 21/6428* (2013.01); *G01N 21/7703* (2013.01); *A61B 5/14552* (2013.01); *A61B 5/15107* (2013.01); *A61B 5/15146* (2013.01); *G01N 2021/0325* (2013.01); *G01N 2021/6484* (2013.01)

(58) Field of Classification Search
CPC . A61B 5/157; A61B 5/150511; A61B 5/1411; A61B 5/150389; G01N 21/7703; G01N 2021/772; A61M 25/065
USPC .......................................... 600/345, 347, 365
See application file for complete search history.

(56) References Cited

U.S. PATENT DOCUMENTS

| | | | |
|---|---|---|---|
| 4,403,984 A * | 9/1983 | Ash et al. .................. 604/503 |
| 4,622,974 A * | 11/1986 | Coleman et al. ............ 600/342 |
| 4,627,445 A * | 12/1986 | Garcia et al. ............... 600/583 |
| 4,687,000 A | 8/1987 | Eisenhardt et al. |
| 4,727,730 A * | 3/1988 | Boiarski et al. ............ 600/480 |
| 4,981,779 A * | 1/1991 | Wagner ..................... 435/287.9 |
| 4,994,073 A | 2/1991 | Green |
| 5,054,882 A * | 10/1991 | Riccitelli et al. ............ 385/12 |
| 5,165,418 A | 11/1992 | Tankovich |
| 5,281,395 A | 1/1994 | Markart et al. |
| 5,368,047 A | 11/1994 | Suzuki et al. |
| 5,390,671 A * | 2/1995 | Lord et al. ................. 600/347 |
| 5,424,035 A | 6/1995 | Hones et al. |
| 5,425,717 A * | 6/1995 | Mohiuddin ................ 604/160 |
| 5,568,806 A * | 10/1996 | Cheney et al. ............. 600/373 |
| 5,586,553 A * | 12/1996 | Halili et al. ............... 600/316 |
| 5,636,640 A * | 6/1997 | Staehlin .................... 600/577 |
| 6,014,577 A | 1/2000 | Henning et al. |
| 6,036,919 A | 3/2000 | Thym et al. |
| 6,192,168 B1 * | 2/2001 | Feldstein et al. ............ 385/12 |
| 6,228,100 B1 | 5/2001 | Schraga |
| 6,358,748 B1 | 3/2002 | Weiss |
| 6,584,335 B1 | 6/2003 | Haar et al. |
| 7,396,334 B2 * | 7/2008 | Kuhr et al. ................. 600/583 |
| 7,654,956 B2 * | 2/2010 | Brister et al. .............. 600/365 |
| 2002/0099415 A1 * | 7/2002 | Panescu et al. ............. 607/24 |
| 2003/0153939 A1 | 8/2003 | Fritz et al. |
| 2003/0157724 A1 | 8/2003 | Petrich et al. |
| 2004/0133164 A1 * | 7/2004 | Funderburk et al. ......... 604/134 |
| 2004/0138562 A1 * | 7/2004 | Makower .......... A61M 25/0084 600/439 |
| 2004/0147811 A1 * | 7/2004 | Diederich ............ A61M 25/10 600/207 |
| 2005/0201897 A1 | 9/2005 | Zimmer et al. |
| 2005/0214891 A1 | 9/2005 | Horn et al. |
| 2006/0122536 A1 * | 6/2006 | Haar .................. A61B 5/14514 600/581 |
| 2007/0191696 A1 * | 8/2007 | Mischler et al. ............ 600/310 |
| 2008/0249435 A1 * | 10/2008 | Haar et al. ................. 600/583 |
| 2011/0251482 A1 * | 10/2011 | Kellerman ........... A61B 5/1075 600/424 |

FOREIGN PATENT DOCUMENTS

| | | |
|---|---|---|
| WO | WO 97/42888 | 11/1997 |
| WO | WO 01/00090 A1 | 1/2001 |
| WO | WO 01/60010 A1 | 8/2001 |
| WO | WO 02/100274 A1 | 12/2002 |

\* cited by examiner

INTEGRATED TEST ELEMENT

CROSS-REFERENCE TO RELATED APPLICATIONS

The present application claims priority to PCT Application No. PCT/EP2004/005924 filed Jun. 2, 2004 and German Patent Application No. 103 25 699.7, filed Jun. 6, 2003.

TECHNICAL FIELD

The invention relates to the field of integrated test elements which have a lancing instrument which can be firstly used to make a wound in a skin opening in order to collect a sample, such as for example, blood. The blood flowing out is subsequently taken up by the test element in the process of which it comes into contact with a reagent contained in the test element resulting in an optically detectable change in a test field. The change in the test field is detected by an analytical unit which enables the determination of an analyte present in the blood.

BACKGROUND

In the medical field blood comes primarily into consideration as a sample. In the following reference is made to blood analysis as an example without limiting the generality.

A particularly important field of application in blood analysis is monitoring the blood sugar level of diabetics which is frequently used especially in the analytical field of blood sugar self-monitoring (home monitoring).

Photometric, carrier-bound tests are widely used in this field of application. Such test elements are often used as single-use articles which usually contain a reagent system that reacts irreversibly with an analyte of a sample and results in a characteristic, optically measurable change of the test element.

Conventional test elements that are used for photometric tests are usually in the form of test strips known in the prior art on which a test field is mounted. The test field consists of a reagent system which can fulfil different functions. The sample is applied to the upper side of the test field. After the required reaction time has lapsed, characteristic colour changes are measured by reflection photometry with the aid of an analytical unit in order to analyse the sample. The evaluation device which is provided to evaluate an analytical result, is usually suitable for a very particular type of test elements of a particular manufacturer. The test elements and the evaluation instrument thus form mutually harmonized components and are usually referred to overall as an analytical system. Such analytical systems are described for example in U.S. Pat. Nos. 5,281,395 and 5,424,035, the disclosures of which are each hereby incorporated by reference.

Lancing devices which can be used by the patient to make an opening in the skin are provided in addition to the analytical systems in order to draw a blood sample especially in the home monitoring field. The blood which flows out through the skin opening can be applied to a test element. The described system requires a complex handling by the user in which he must firstly make a wound in order to have a sufficient sample volume for the blood analysis. The site at which the blood emerges is subsequently contacted with the test field of a test element so that sufficient sample can penetrate into the test field. Afterwards the test field containing the sample has to be positioned relative to an analytical unit in order to analyse the test field.

In order to simplify the described complex process for the user, systems are offered in the prior art which combine several working steps.

A blood collecting system is described in the document WO 97/42888 which can be used on the one hand to make a wound in a part of the body so that blood emerges from the body opening for analysis. On the other hand, the blood collecting system is also designed such that a cannula in the system which is arranged near to the lancet and thus near to the site of incision is suitable for taking up blood. Hence the sample can be sucked into the cannula after the lancing process by means of capillary effects and subsequently be delivered onto a test element provided for this purpose containing a reagent system. The test elements used for this are designed in a manner well known in the prior art and are used accordingly. Although the described system simplifies sample application on the test element for the user, separate operating steps are required by the user to transfer the blood from the cannula onto a test field.

The document U.S. Pat. No. 4,360,016 discloses a blood collecting system. In addition to the aforementioned handling steps, the described prior art is also disadvantageous because an increased amount of sample is required in the system. After the sample has been collected and delivered through a cannula, an adequate sample volume must also be available for application to the test field.

An analytical system is also described in the U.S. Pat. No. 4,627,445. For this a skin opening from which blood can emerge is firstly made with a lancet. Due to the prevailing underpressure in the system, the blood is sucked into the analytical system from the blood discharge site through a lateral channel and is passed to a test field. The test field is arranged in the analytical system in such a manner that a measuring unit which is positioned directly above the test field can analyse the test field.

A disadvantage of the described prior art is the very complex design of the analytical system which, among others, requires an underpressure for sample collection. Furthermore, a sufficient volume of sample must emerge from the body opening in order to completely cover the test field after the sample has been conveyed in the transport channel to the test field.

In order to have a sufficient amount of sample for such systems despite the given dead volumes in the transport channels, the piercing depth of the lancet must in principle be correspondingly deep and thus a sufficiently large wound must be selected. However, an increased puncture depth results in increased pain sensation which should be avoided especially in the case of patients who have to draw blood several times daily.

SUMMARY OF THE INVENTION

The blood collection system according to the invention enables a comfortable handling for the user without requiring a larger sample volume.

The system for analysing a sample to be examined comprises a test field containing a reagent which on contact, interacts with an analyte contained in a sample resulting in an optically detectable change in the test field, at least one light-conducting element having a first distal end which is arranged in a region of the test field and a second proximal end into which light can be coupled such that light is conducted from the second end to the test field and is conducted away again from the test field by the same or another light-conducting element, and a lancet having a lancet tip which is located in a region of the distal end and of the test field in such a manner that the lancet tip extends beyond the distal end of the light guide and beyond the test field during a lancing process.

These and other features of the present invention will be more fully understood from the following detailed description of the invention taken together with the accompanying claims. It is noted that the scope of the claims is defined by the recitations therein and not by the specific discussion of the features set forth in the present description.

BRIEF DESCRIPTION OF THE DRAWINGS

Specific embodiments are elucidated in the following on the basis of the figures.

Figure 1:
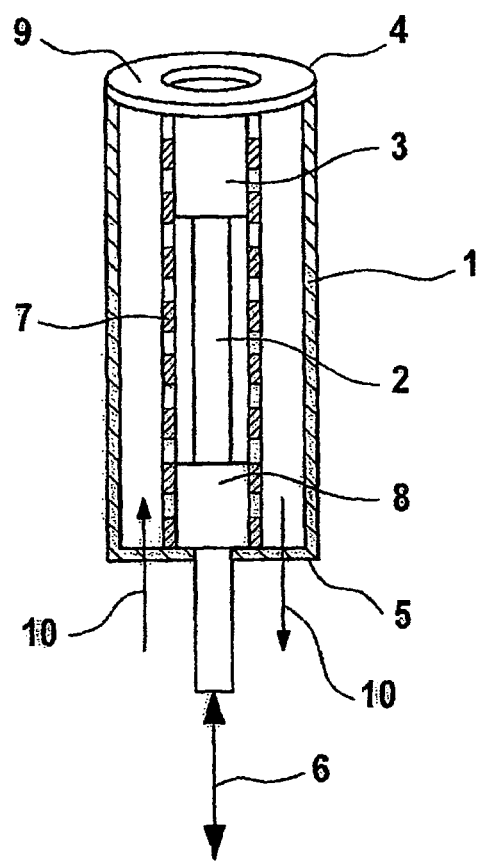
FIG. 1: System with a light-conducting hollow fibre

In order that the invention may be more readily understood, reference is made to the following examples, which are intended to illustrate the invention, but not limit the scope thereof.

DETAILED DESCRIPTION OF THE DRAWINGS

The invention is characterized by a system which is suitable for collecting and analysing a sample to be examined. The system comprises a test field containing a reagent which reacts when it comes into contact with the analytes present in the sample and results in an optically detectable change in the test field. The system also comprises a lancet with a lancet tip. According to the invention the system has at least one light-conducting element. A first distal end of the light-conducting element is arranged in the area of the test field and light can be coupled into a second proximal end of the light-conducting element such that light is guided from the second end to the test field and can again be guided away from the test field by the light-conducting element or another light-conducting element. For this the lancet, the test field and the at least one light-conducting element are arranged relative to one another in such a manner that the lancet tip projects beyond the distal end of the light-guide and beyond the test field during a lancing process. In order to collect the sample, the test field is contacted with the sample during which the distal end of the light-conducting element is positioned essentially directly at the site of sample collection.

The system according to an embodiment of the invention enables the sample to be taken up directly by the test field at the site of sample collection without requiring additional transport channels for this. Hence the sample collection site of the system is realized by the test field and thus the sample does not have to be transported to a test field in the system. The position of the test field and thus of the sample collection site relative to an analytical unit in an analytical system can be selected as desired and should be provided at a site which is readily accessible to the user. An analytical unit for measuring the test field and the test field are optically contacted according to the invention by at least one light-conducting element so that the test field and analytical unit can be positioned relative to one another in a flexible manner. This allows the required volume of sample for analysis to be reduced since there are no dead volumes due to transport channels and, on the other hand, the design of an analytical system which is suitable for using the system according to the invention can be accordingly comfortably adapted to the user requirements.

The integration of a light-conducting element into the system according to the invention enables the test field to be directly measured, provided the light-conducting element is optically contacted with an analytical unit, without the user having to position the test field relative to an optical system in an analytical instrument after sample collection. Hence the test field can also be evaluated by a suitable analytical instrument outside the analytical instrument thus enabling a so-called outside dosing for an integrated photometric analysis. In this case a first section of the light-conducting system is usually located within the instrument whereas a second section i.e. the distal end of the light-guide protrudes from the instrument and is thus readily accessible for the user. Contamination of the instrument during blood application to the test field positioned at the distal end can thus be avoided. Moreover, the design of an analytical system can be greatly simplified since no special requirements are made on the positioning of the optical system in the analytical system. The system can be coupled to the analytical instrument in a conventional manner without requiring complex or unusual handling steps by the user. According to the invention the system and analytical instrument are optically contacted in this process thus automatically ensuring a positioning of the test field relative to the optical system.

Within the scope of the invention, the region of the test field in which the distal end of the light-conducting element is positioned is characterized in that the test field and the distal end are arranged relative to one another such that an optical contact between the test field and light-conducting element is possible. In general the system is not limited to a special embodiment of a test field, and according to the invention the arrangement of test field and distal end allows a measurement of the test field by light which is transported to the test field and conducted away from the test field by means of the light-conducting element. In this connection the test field can for example be directly mounted on the light-conducting element or only be disposed thereon.

If, in an embodiment, the test field is permanently connected to the light guide, a reagent layer can for example be glued or sprayed onto the distal end of the light guide or be applied by photopolymerization for this purpose. The photopolymerization process is described for example in U.S. application Ser. No. 10/514,758 filed Nov. 16, 2004, the disclosure of which is incorporated herein by reference.

If, in contrast, the test field is designed to be reversibly positioned relative to the light guide, this for example allows an integration of a test strip tape into the system according to the invention as described in the prior art in the document U.S. application Ser. No. 11/124,591, filed May 6, 2005 (Publication No. US-2005-0201897-A1), the disclosure of which is incorporated herein by reference. For this purpose the distal end of the light guide is reversibly positioned at a test field on a tape such that the test strip tape that is elucidated in more detail in the following can be movably guided below the light-conducting element.

In principle the system according to the invention can for example contain several test fields on which the light-conducting element is reversibly arranged without being permanently connected to them. The test field is then discarded after single use, whereas the light-conducting element is designed for multiple use and in each case is positioned anew at a test field provided for measurement. In this case the test fields are arranged on a separate support in the system; as already elucidated on the basis of a test strip tape. The system according to the invention can also contain a plurality of lancets which are replaced by the user as and when required so that all possible combinations of a system are conceivable in which the system for example comprises several test fields and/or several lancets and at least one light-conducting element.

Since the structure of the test field does not have to meet any special requirements, it is for example possible to use single or multilayered test fields, which are adequately well known from the prior art. According to the invention an optically detectable change in the test field occurs after a sample has been applied thereto. For example it is also possible to use test fields which are for example known in the prior art from test strips with sample preparation functions. Such a test field has a multilayered structure and can be used in particular to facilitate a uniform wetting of the test field with the sample liquid. As a result of the multilayered structure it is for example possible to separate red blood corpuscles from whole blood in an upper layer so that only plasma reaches the lower region of the test field in which a reaction with a reagent takes place. The evaluation of the measured signal i.e. the measured intensity of the light conducted away from the test field and the determination of the desired analytical results, for example the glucose concentration in the sample, is carried out by the measuring and evaluation electronics basically in the same manner as with common analytical systems and does not therefore have to be elucidated in more detail here.

If the optically detectable change that is induced in the test field is picked up by the light-conducting element and detected and evaluated by an analytical unit, this can be achieved for example by photometrically evaluating the radiation reflected from the test field. However, it is also possible to arrange the light-conducting element and the test field relative to one another such that the optically detectable change in the test field is measured in transmission. The measuring arrangement and test field must then be suitably designed for a transmission measurement. In an embodiment it is evaluated by fluorescence measurements. In this case a single light guide can be used for the irradiation as well as for the emission. The excitation radiation is essentially eliminated by a suitable filter in front of a detector of an analytical unit to such an extent that no overlap occurs between the irradiation and emission in order to achieve a high accuracy of the measurement.

The light-conducting element of the system is made of a material which is substantially transparent in the wavelength range of the irradiated light which is coupled into the second end of the light guide in order to analyse the sample so that essentially no optical absorption occurs. The refractive index of the material is larger than the refractive index of the surroundings so that a total reflection occurs within the light-conducting element. In principle it is also conceivable that the light within the light-conducting element is based on a metallic reflection on one of the interfaces bordering the light-conducting element. More detailed information on light-conducting elements whose light transport is based on total reflection may be found in the relevant literature, such as for example, the use of light guides in a test strip is described in the document US 2003/0157724 A1, Aug. 21, 2003, the disclosure of which is hereby incorporated by reference.

In an embodiment, light which is also referred to as primary light in the following is conducted under the condition of total reflection to the first end of the light-conducting element where the light is coupled out into the test field. In this connection the primary light is for example either guided directly onto the test field or it is firstly deflected from the light-conducting element into the test field. A change in the direction of light propagation can for example be achieved by a reflecting surface which is for example tilted at an angle of about 45°. Such a reflecting property can for example be achieved by a metallic shining coating or a polished surface etc. In principle it is possible to use various means to effect the desired light coupling out of the light-conducting element into the test field. In particular the refractive index of the environment and that of the light-conducting element in the area where light is coupled out can be designed such that total reflection essentially no longer occurs. Furthermore, the coupling out can be facilitated by roughening the surface of the light-conducting element in the region where the light is coupled out. In addition the light can be coupled out by a suitable light guidance within the light-conducting layer which is such that at least a major portion of the primary light in the coupling-out region impinges on the facing interface in the test field at an angle which is larger than the critical angle for total reflection. For example the distal end of the light-conducting element is slanted for this purpose in such a manner that the primary light is reflected in the test field.

The secondary light that is diffusely reflected, emitted or transmitted from the test field is subsequently coupled into the light-conducting element and conducted away from the test field under total reflection. In this connection the light-conducting element is basically, at least in sections, designed such that the direction of light propagation of the irradiated primary light is guided towards the test field and/or the direction of light propagation of the secondary light that is diffusely reflected, emitted or transmitted from the test field is deflected into the direction of the light-conducting element leading to the detector.

Basically it is possible that the primary light and the secondary light is transported in a light-conducting element. However, especially in the case of measurements in reflection it has proven to be advantageous to integrate at least two light-conducting elements into the system such that the primary and secondary light can be transported separately from one another. If two light-conducting elements are used, the primary light guide and the secondary light guide can be optically accomplished in a substantially separate manner. An optical separation of the primary light guide and secondary light guide that is as complete as possible proves even to be an important prerequisite with regard to an optimal measurement accuracy. For this purpose it is for example possible to provide a light barrier which is for example in the form of a barrier layer whose refractive index is less than the refractive index of the light-conducting element. Furthermore, the optical separation can be accomplished by using a barrier layer formed from a metallic reflecting material.

In order to facilitate a targeted coupling of the secondary light into a second light-conducting element, sections of the secondary light guide are bevelled in an embodiment in such a manner that the secondary light is reflected by a reflecting surface in the secondary light guide. The angle of inclination of the reflecting surface is, for example, in the angle range of about 45°.

The secondary light that is conducted away by the system is registered by a detector in an analytical instrument thus enabling a determination of an analyte present in the sample on the basis of the signal. In order to couple the secondary light out of the light-conducting element towards the detector, an inclined, reflecting surface is for example in turn provided at the rear end of the light-conducting element. Instead of the reflecting surfaces it is in principle also possible to use other means to effect the desired change in the direction of light propagation. This is achieved in particular by varying the refractive index of the light-conducting element. Such variations in the refractive index can for example be achieved by irradiation with UV laser light.

The light registered by the detector is essentially free of interfering primary light components so that a good signal-to-noise ratio is achieved.

If the measurement is carried out in reflection, experiments have shown that, in comparison to conventional measurements in which no light-conducting elements are used, a higher proportion of the detected secondary light that is diffusely reflected by the test field can be registered as a signal thus resulting in an increase in the measurement accuracy of the method. In order to further optimize the accuracy of the measurement, the test field can additionally contain components which scatter the light strongly.

Thus in addition to a considerable simplification of the handling steps for the user and a simple system design, the system also enables an increased accuracy of the measurement.

The system according to the invention is used as a single-use article in a lancing device where the reagent present in the test field essentially irreversibly reacts with an analyte of the sample. The chemistry used as the reagent is sufficiently well-known in the prior art and hence no further elucidation is made here. For example, U.S. Pat. No. 6,036,919, the disclosure of which is hereby incorporated by reference, describes a chemistry that irreversibly reacts with an analyte of a sample. In an embodiment, the test field contains a substance which changes its fluorescence when it reacts with the analyte. Such reagent systems are described in the prior art for example in the document U.S. application Ser. No. 10/514,451, Filed Nov. 15, 2004 (Publication No. US-2005-0214891-A1), the disclosure of which is incorporated herein by reference.

As a result of using the system as a single-use article and the possibility of so-called outside dosing, it is possible to avoid contamination of a sample by previous analyses.

The system according to the invention is used in a lancing device which has a drive unit for the lancet of the system such that the lancet is coupled to the drive unit and can be moved in the direction of lancing.

In an embodiment, an analytical unit is additionally integrated into the lancing device which is optically contacted with the light guide of the system when the system is placed in the lancing device. According to the invention the optical contacting occurs in such a manner that light can be coupled into the light-conducting element and the light conducted away from the test field can be detected by the analytical unit. The coupling of the light-conducting element to a lancing device containing an analytical unit automatically positions the test field relative to the optical measuring system such that the test field is always present and can be measured in a measuring position. An optical contacting between an analytical instrument and a test element described in the document US 2003/0157724 A1, Aug. 21, 2003, the disclosure of which is hereby incorporated by reference. A lancing device equipped in this manner may be regarded as a fully adequate analytical system and hence the user only has to operate a single instrument in order to carry out the analysis.

In order to measure an analyte, the user firstly places the analytical system on the body part e.g. the fingertip where he triggers the lancing process. The lancet is then moved in the lancing direction by the drive unit such that the lancet tip penetrates into the fingertip where it makes a wound. The blood emerging from the wound is subsequently contacted with the test field which is positioned essentially in the area of the puncture site.

If, in an embodiment, the test field is rigidly connected to the light guide, the light guide can in addition to the lancet also for example be moved by the drive unit or another drive unit in the lancing device so that the test field can be directly moved to the wound after the lancing process. This improves the sample collection. If, on the other hand, these additional measures are omitted, experiments have shown that sample collection by the system is adequate even without an additional guidance of the test field. This is demonstrated in particular by an embodiment in which the lancet is arranged in a plane essentially perpendicular to the direction of puncture directly adjacent to the light guide or to the test field. Thus the puncture site as well as the site of measurement and/or sample collection are in direct vicinity to one another in a plane essentially perpendicular to the lancing direction. Consequently the test field and the end of the light guide are positioned essentially directly at the wound after the lancing process. The test field is subsequently measured directly at the site of sample collection. This saves the user from carrying out any additional operating steps provided an evaluation is performed directly by the lancing device. The user is then informed directly about the analytical result by means of a display on the lancing device. After the analytical system has been used, the system is removed from the lancing device or exchanged.

Of course embodiments are also conceivable in which the system is separately connected to an analytical unit. If the analytical unit is not directly integrated into the lancing device, the lancing device can for example be connected to the system on an analytical instrument provided for this purpose. In this case the lancing device has an appropriate coupling mechanism which optically contacts the analytical unit via the lancing device with the system. It is of course also conceivable that the system after it has been removed from the lancing device can be directly coupled to an analytical unit that is suitable for this purpose. However, the aim is to substantially spare the user separate operating steps so that in an embodiment the user can directly read the analytical result on a highly integrated analytical system after the lancing process has been triggered.

For this purpose the lancing device contains measuring and evaluation electronics in an embodiment such as those that are well-known in the prior art. A light-emitting diode (LED) is for example connected to the measuring and evaluation electronics which, as a light emitter, couples the primary light into the light-conducting element of the system. The secondary light that is conducted away by the system is for example registered by means of a photodiode which, as a detector, is a component of the optical measuring device.

In order to further simplify the handling for the user, a lancing device can contain a plurality of systems which are stored in a storage container and are successively provided to the user for use. In this case it is conceivable to integrate a large variety of embodiments of the system according to the invention as already described in which the system for example has a plurality of test fields and/or lancets. An appropriate loading into magazines is then carried out such that for example it is also only possible to load individual elements of the system such as test fields and/or lancets into a magazine. The system or individual elements thereof are reloaded into a magazine within the storage container or an additional waste container after use to ensure a comfortable disposal of used system/elements after each lancing process. This ensures a safe and hygienic disposal as well as handling of the system. Storage in magazines within a lancing device can, as described above, occur in a wide variety of ways and is well-known in the prior art. For example embodiments can be designed similar to the storage of test elements in magazines as described in U.S. application Ser. No. 11/178, 810, Filed Jul. 11, 2005, the disclosure of which is hereby incorporated herein by reference.

The system can be realized in various ways according to the invention. In an embodiment the tip of the lancet and the test field are arranged concentrically relative to one another, the lancet for example being surrounded at least partially by the light-conducting element and guided within a hollow light-conducting fibre. The integration of the lancet into the hollow fibre enables the lancet to be moved to and fro in the lancing direction relative to the light guide in such a manner that the lancet tip only protrudes from the hollow fibre during a lancing process. Hence the lancet tip is surrounded by the hollow fibre in a protective manner after and before the puncture. In this manner additional functions such as a sterile protection of the lancet tip and a protection of the user from injury on the lancet tip can be easily integrated into the system. In order to ensure the sterility of the lancet tip in the system it is of course possible to utilize additional measures, a non-limiting example of which includes that disclosed in US2003153939 (A1), Aug. 14, 2003, the disclosure of which is hereby incorporated by reference.

Furthermore, complementary embodiments are also conceivable in which the lancet at least partially surrounds the light-conducting element and the light guide is for example arranged within a hollow lancet. The lancing device then, as already mentioned above, has a drive unit for the light-conducting element.

FIG. 1 shows a system in which a light-conducting hollow fibre (1) is arranged concentrically around a lancet (2). The hollow fibre has a proximal end (5) into which light from an analytical unit (not shown) can be coupled in or out. The element has a reagent layer (9) at a distal end (4) of the light guide which was attached to the light guide by gluing or polymerization and is permanently joined thereto. Hence the lancing site and the test field are arranged concentrically relative to one another, the test field surrounding the lancet tip in a circular manner. The outer diameter of the system is a few mm in the example shown. The lancet tip (not shown) is embedded in a sterile protection (3) which ensures the sterility of the lancet. When the lancing process is carried out, the lancet tip pierces the elastic sterile protection so that the lancet tip protrudes from the sterile protection and extends beyond the distal end (4) of the light guide (1) and beyond the test field (9) during the lancing process. After the lancing process, the lancet tip is retracted again into its resting position in the hollow fibre where it is surrounded in a protecting manner by the sterile protection (3). The system also has a guide element (8) formed from plastic which securely guides the lancet (2) within the hollow fibre during the lancing process in a low-vibration manner. For this purpose the lancet is moved forwards or backwards in the direction of puncture (6) relative to the light guide. If sample has been applied to the test field (9), the light (10) is firstly guided to the test field where it interacts with the analyte-reagent complex in the sample. Subsequently the light is diffusely reflected from the test field into the hollow fibre or is emitted as fluorescence and guided by means of total reflection within the light guide to a detector (not shown). An optically detectable change in the test field (4) due to an analyte can thus be detected and measured. Such a system is for example used to analyse a glucose concentration in a sample.

In an embodiment, the system is provided as a single-use article. In this case the test field (4) usually contains a reagent that irreversibly reacts with an analyte in the sample. After single use the system is discarded.

Figure 2:
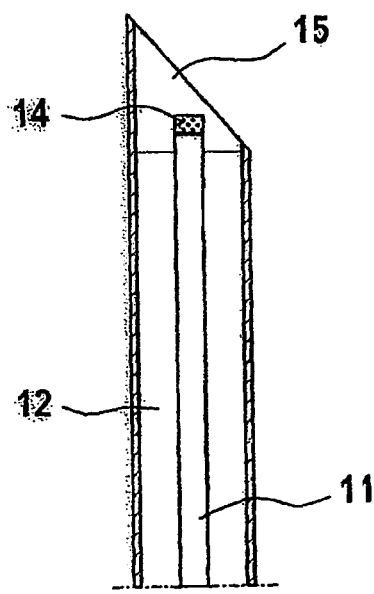
FIG. 2: System with a hollow cannula

FIG. 2 shows a complementary embodiment of the system described above. The system has a hollow cannula (12) within which a light-conducting element (11) is located. The distal end of the light-conducting element is also coated with an analyte-specific reagent (14) and thus forms the test field. The hollow cannula has a tip which is suitable for making an opening in the skin. The upper region of the hollow cannula has an opening (15). If a wound has been made by the hollow cannula in a body part of a patient, the opening (15) enables the distal end of the light guide and thus of the test field to be contacted with the sample. It has turned out that an additional guidance of the light-conducting element relative to the hollow cannula facilitates sample uptake by the test field. For this purpose the distal end of the light guide is moved out of the opening (15) after the lancing process until it protrudes beyond the tip of the lancet. Contact between the test field and the blood of the patient is thus easily achieved.

Figure 3A:
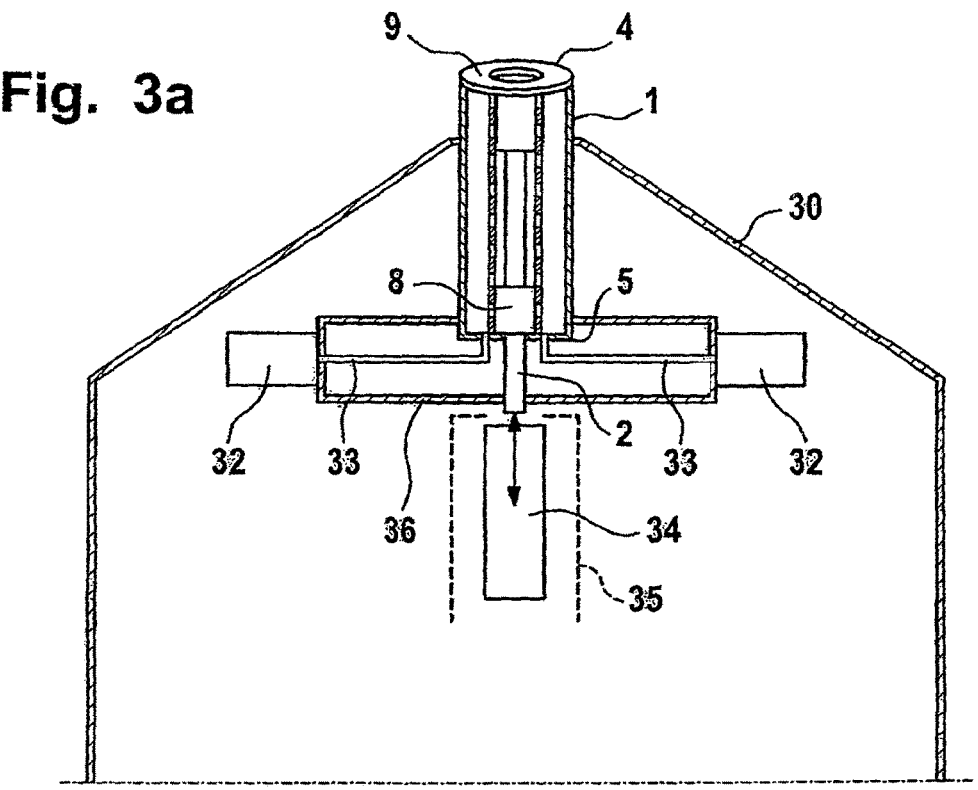
FIG. 3: Analytical system

FIG. 3 shows a schematic drawing of an analytical system which is realized in a lancing device. The lancing device has an analytical unit (32) to evaluate the system and a drive unit (34) to couple the lancet to the lancing device.

FIG. 3 shows essentially an integration of a system similar to FIG. 1 which has a light-conducting hollow fibre (1) which is arranged concentrically around the lancet (2). In order to carry out a lancing process, the lancet (2) is moved in the direction of lancing by the lancet drive (34) such that the lancet tip (not shown) extends beyond the distal end of the hollow fibre and can make a wound in a fingertip placed there. Subsequently the lancet is again retracted by the drive unit during which the guide element (8) ensures a low-vibration execution of the lancing process. In order to analyse the test field, light is coupled into the proximal end of the hollow fibre by means of an analytical unit (32). For this purpose the analytical unit (32) has a light emitter which is coupled to the system via further additional light-conducting elements (33). In this case the light-conducting elements (33) which are located permanently in the lancing device are optically coupled to the light-conducting hollow fibre of the system which is designed as a single-use article. Light can thus be guided through the light-conducting hollow fibre (1) to the distal end (4) of the hollow fibre and thus to the test field (9) according to the system shown in FIG. 1. Irradiation of the test field excites a fluorescence radiation depending on the analyte present in a sample. Light emitted in this manner is coupled out of the hollow fibre by means of the light-conducting element (33) and conducted to a detector of the analytical unit (32).

In addition it is conceivable that an additional drive unit (35) is provided which is coupled to the hollow fibre and also guides it in the direction of lancing to the site at which blood emerges in order to improve the sample collection after the lancing process. If the system is then positioned essentially completely within the housing (30) of the lancing device, only the lancet firstly emerges from the housing (30) during the lancing process. After the puncture the distal end of the hollow fibre is then moved accordingly to the wound by the drive (35) in order to facilitate sample collection.

However, in the example shown the drive unit (35) for the hollow fibre which is indicated schematically is omitted so that instead the hollow fibre is positioned stationary in a holder (36) within the analytical system. After the system according to the invention has been used once it can be removed by the user from the holder (36) in the lancing device and exchanged. When the system is again inserted into the holder (36) the hollow fibre is automatically optically coupled to the light-conducting element or elements (33) and mechanically coupled to the drive unit or units.

The drive units (34) and/or (35) can in principle be coupled to the lancet or to the light-conducting element in a variety of ways and in an embodiment is designed such that the elements can be moved in the direction of puncture as well as in the reverse direction. For example such a coupling of the drive unit/s can be achieved by a form-fitting coupling to the lancet and/or to the hollow fibre which are designed in an appropriate manner. Such a form-fitting coupling which is especially suitable for integrated systems is described for example in the document U.S. application Ser. No. 11/178,810, filed Jul. 11, 2005, the disclosure of which is hereby incorporated herein by reference.

Figure 3B:
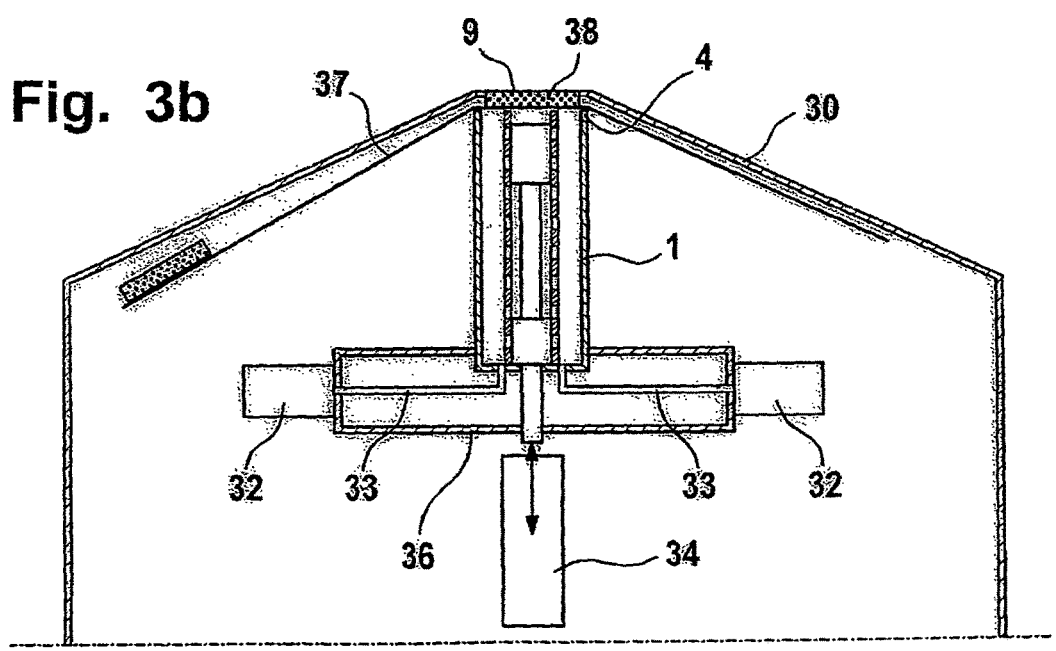

FIG. 3b shows an analytical system according to the invention in which the light-conducting element in the form of a hollow fibre (1) is reversibly positioned at the test field (38). The system according to the invention is coupled to the analytical instrument in a similar manner to the embodiments shown in FIG. 3a. Hence the analytical system also has an analytical unit (32) and a drive unit (34) for the lancet in its housing (30). The hollow fibre (1) is held stationary in the analytical system by means of the holder (36). The distal end (4) of the hollow fibre is reversibly positioned on a transparent carrier tape (37) such that the carrier tape can be movably guided along the distal end of the light guide. At regular intervals the carrier tape has regions that are coated with the reagent and thus form the test field (9). In this connection the thin carrier tape is firstly located between the distal end of the light guide and the skin. The prick is either made directly through the carrier tape or through a pre-formed hole therein. Directly after the prick the carrier tape is moved further such that a test field comes to rest between the light guide and skin and can in this position take up the discharged sample. Hence, sample collection by the system can also be improved by a guided movement of the test field without it having to be permanently connected to the light guide. Alternatively a test field position on the carrier tape can also already be positioned between the light guide and skin during the lancing process. The prick is then expediently made through a hole in the test field or directly through the test field.

The hollow fibre in FIG. 3b does not have to be replaced and can be used as a permanent component of the analytical system. It is also conceivable to design the lancet for multiple use but usually wear of the lancet tip has to be expected. Then only the test fields would be initially provided in the analytical system for a single use. As a result of using a test strip tape which is elucidated in more detail on the basis of FIG. 4, the tape and thus the test field can be simply transported further after use along the distal end of the hollow fibre until an unused test field is again available for blood collection. In this manner the user can simply carry out a blood analysis without having to exchange elements of the analytical system before each use. If the test field tape and the lancet are suitable for multiple use, this enables a comfortable and inconspicuous handling of the analytical system by the user.

Figure 4A:
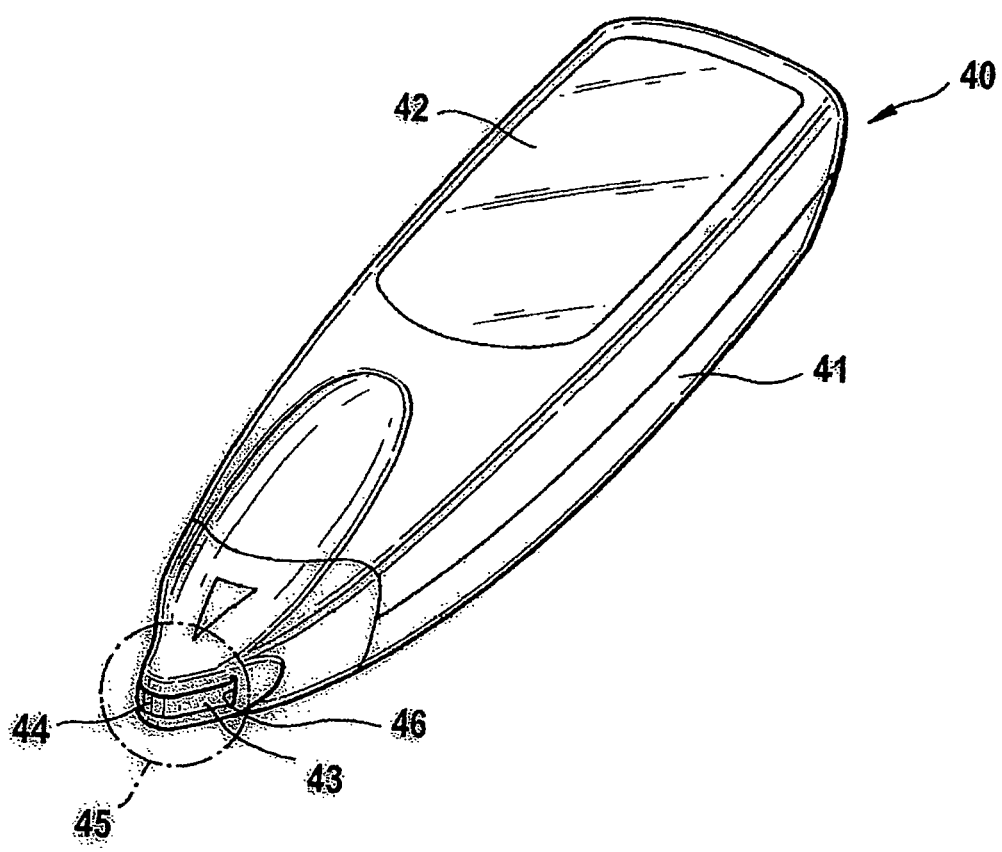
FIG. 4: System with a test field tape Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.
Figure 4B:
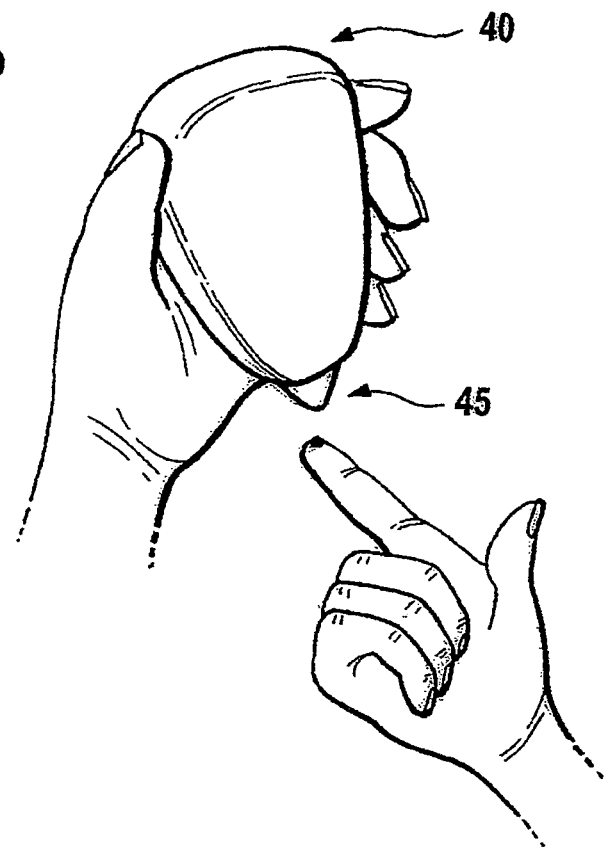
Figure 4C:
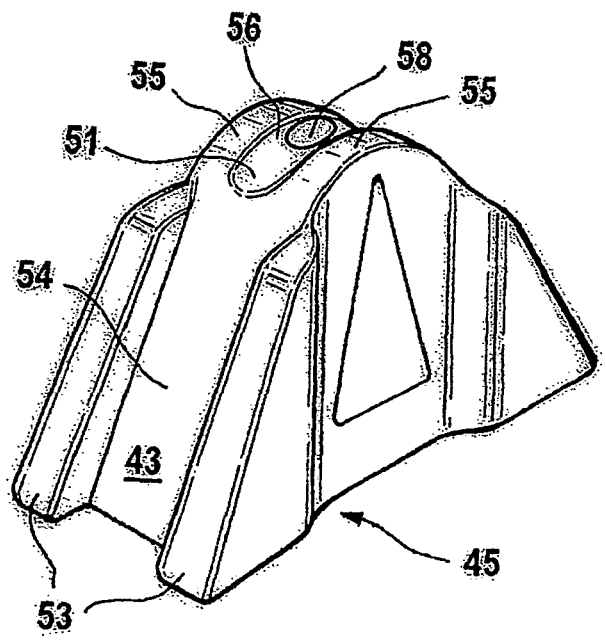

FIGS. 4a to 4c show an analytical system in which several test fields are arranged on a tape cassette. The analytical system (40) has a housing (41) which is constructed in a form which is easy to handle by the user. The housing has an opening (46) in a pointed front end (45) of the analytical system from which a test field tape (43) emerges. In order to realize an analytical system with a test field tape reference is made to the document U.S. application Ser. No. 11/124,591, Filed May 6, 2005, Publication No. US-2005-0201897-A1, the disclosure of which is hereby incorporated by reference. The test field tape (43) has areas (44) at periodical intervals which are coated with a reagent chemistry and thus form a test field (44). In order to carry out a lancing process the front end (45) of the analytical system (40) is placed on the fingertip of a patient. In doing so the test field tape is positioned such that a test field (44) rests directly on the front end (45) of the analytical system.

For a more detailed illustration the front end (45) of the analytical system is enlarged in FIG. 4(c). It can be seen that the test field tape is guided within guide rails (53) of the front end (45). The area of the test field tape which forms the test field has a hole (56). The test chemistry of the test field is applied to an outer area (55) which surrounds the hole (56). In the remaining areas (54) of the test field tape in which no test field is provided, the tape is formed in one piece. This stabilizes the guidance of the tape within the analytical system. The front region (45) of the analytical system also has a hole (58) at its front end which is placed in a contact surface (51). In order to carry out the lancing process, a lancet emerges through the hole (58) and the hole (56) of the test field to make a wound in a fingertip resting thereon. After the lancing process the blood emerging from the wound is taken up by the test field areas (55) where it interacts with the reagent contained in the test field. The contact surface (51) on which the test field rests during the lancing and measuring process and the test field tape are optically transparent. The test field can be measured at the site of sample collection with the aid of two light-conducting elements which are arranged within the analytical system directly at the contact surface (51). After analysing the sample the test field tape is transported further in accordance with the principle of a tape cassette as described in the document U.S. application Ser. No. 11/124,591, Filed May 6, 2005 (Publication No. US-2005-0201897-A1), which is hereby incorporated herein by reference, until the next test field is positioned above the contact surface (51). The analytical system is now again ready to carry out a lancing and measuring process. For this purpose the system for example has a plurality of lancets. The user is informed about the result of the analysis via the display (12).

Having described the invention in detail and by reference to specific embodiments thereof, it will be apparent that modification and variations are possible without departing from the scope of the invention defined in the claims. More specifically, although some aspects of the present invention are identified herein, it is contemplated that the present invention is not necessarily limed to these one aspects of the invention.

What is claimed is:

1. A monitoring system for analysing a sample to be examined comprising
a test field containing a reagent which on contact, interacts with an analyte contained in a sample resulting in an optically detectable change in the test field, wherein the reagent is configured to irreversibly react with the analyte, wherein the reagent is configured to analyse glucose concentration;
at least one light-conducting element having
a distal end on which the test field is coated, wherein the test field is permanently adhered to form a layer on the distal end and
a proximal end into which light can be coupled such that light is conducted from the proximal end to the test field and is conducted away again from the test field by the same or another light-conducting element;
a lancet which at least partially surrounds the light-conducting element having a lancet tip which is located in a region of the distal end and of the test field in such a manner that the lancet tip extends beyond the distal end of the light-conducting element and beyond the test field during a lancing process, wherein the lancet has an opening that enables the test field on the distal end of the light-conducting element to protrude beyond the lancet tip for contacting the sample, wherein the opening of the lancet is unobstructed to allow the test field on the distal end of the light-conducting element to protrude beyond the lancet tip, wherein the lancet tip is sharpened to pierce skin to form a wound in skin; and
a driver configured to move the test field on the distal end of the light-conducting element from a first position where the test field is located inside the lancet to a second position where the test field on the distal end of the light-conducting element protrudes beyond the lancet tip for contacting the sample of blood emerging from the wound on the surface of the skin after the wound is formed for reducing dead space issues.

2. The monitoring system as claimed in claim 1, which has a plurality of test fields.

3. The monitoring system as claimed in claim 1, which has a plurality of lancets.

4. The monitoring system as claimed in claim 1, which is suitable only for single use.

5. The monitoring system of claim 1, wherein:
the at least one light-conducting element includes a primary light guide configured to conduct primary light onto the test field and a secondary light guide configured to conduct secondary light that is reflected from the test field; and
wherein the primary light guide and the secondary light guide are optically separated to enhance measurement accuracy.

6. The monitoring system of claim 5, wherein the primary light guide and the secondary light guide are optically separated by a barrier layer that has a refractive index that is less than the refractive index of the light conducting element.

7. The monitoring system of claim 6, wherein the barrier layer includes a metallic reflecting material.

8. The monitoring system of claim 1, wherein the test field is uncovered on the distal end.

9. A monitoring system for analysing a sample to be analysed comprising
a test field containing a reagent which on contact, interacts with an analyte contained in a sample resulting in an optically detectable change in the test field, wherein the reagent in the test field reacts essentially irreversibly with the analyte;
at least one light-conducting element having
a distal end which is permanently connected to the test field, wherein the test field is permanently adhered to form a layer on the distal end, and
a proximal end into which light can be coupled such that light is conducted from the second end to the test field and is conducted away again from the test field by the same or another light-conducting element;
a lancet having a lancet tip which is located in a region of the distal end and of the test field in such a manner that the lancet tip extends beyond the distal end of the light guide and beyond the test field during a lancing process, the lancet being hollow, wherein the light-conducting element extends within the lancet, wherein the lancet has an opening that enables the test field on the distal end of the light-conducting element to protrude beyond the lancet tip for contacting the sample, wherein the lancet tip is configured to create a wound, wherein the lancet tip is embedded in a sterile protection; and
a driver configured to move the test field on the distal end of the light-conducting element from a first position where the test field is located inside the lancet to a second position where the test field on the distal end of the light-conducting element protrudes beyond the lancet tip for contacting the sample on the surface of skin after the wound is formed for reducing dead space issues, wherein a side of the test field opposite the distal end of the light-conducting element is configured to directly contact the sample bled from the wound when in the second position.

10. The monitoring system as claimed in claim 9, which is suitable only for single use.

11. The monitoring system as claimed in claim 9, which has a plurality of test fields.

12. The monitoring system as claimed in claim 11, which has a plurality of lancets.

13. The monitoring system as claimed in claim 9, in which the lancet and the light-conducting element are arranged concentrically relative to one another.

14. The monitoring system as claimed in claim 9, in which the lancet and the light-conducting element are arranged in direct vicinity to one another in a plane perpendicular to the lancing direction.

15. The monitoring system as claimed in claim 9, which is suitable for determining a glucose concentration from blood.

16. The monitoring system as claimed in claim 9, which can be optically contacted with an analytical unit of an analytical instrument such that light is coupled into or out of the light-conducting element.

17. The monitoring system as claimed in claim 9, which is used in a lancing device.

18. The monitoring system as claimed in claim 17,
in which the lancing device comprises an analytical unit which is optically contacted with the light-conducting element in such a manner that light can be coupled into the light-conducting element and the light conducted away from the test field can be detected by the analytical unit.

19. The monitoring system as claimed in claim 17,
in which the lancing device can be coupled to an analytical unit such that
light can be coupled into the light-conducting element and the light conducted away from the test field can be detected by the analytical unit.

20. The monitoring system as claimed in claim 17, in which the lancing device comprises a drive unit for the lancet.

21. The monitoring system as claimed in claim 20, in which the lancing device contains a drive unit for the light-conducting element.

22. The monitoring system as claimed in claim 17, in which the lancing device contains a drive unit for the light-conducting element.

23. The monitoring system as claimed in claim 22, in which the lancing device contains a drive unit for transporting the test element.

24. The monitoring system as claimed in claim 17, in which the lancing device contains a drive unit for transporting the test element.

25. The monitoring system as claimed in claim 17, which is positioned in a magazine of the lancing device in which a plurality of systems is located.

26. The monitoring system of claim 9, wherein the lancet tip is sharpened to pierce skin.

\* \* \* \* \*